(12) United States Patent
Keller

(10) Patent No.: US 8,460,235 B2
(45) Date of Patent: Jun. 11, 2013

(54) DISPENSING ASSEMBLY FOR TWO COMPONENTS WITH DOUBLE SYRINGE AND MIXER

(75) Inventor: Wilhelm A. Keller, Merlischachen (CH)

(73) Assignee: Medmix Systems AG, Rotkreuz (CH)

( * ) Notice: Subject to any disclaimer, the term of this patent is extended or adjusted under 35 U.S.C. 154(b) by 0 days.

(21) Appl. No.: 12/452,017

(22) PCT Filed: Jun. 9, 2008

(86) PCT No.: PCT/CH2008/000261
§ 371 (c)(1),
(2), (4) Date: Dec. 11, 2009

(87) PCT Pub. No.: WO2008/151456
PCT Pub. Date: Dec. 18, 2008

(65) Prior Publication Data
US 2010/0121268 A1 May 13, 2010

(30) Foreign Application Priority Data
Jun. 13, 2007 (CH) ........................................ 0938/07

(51) Int. Cl.
*A61M 37/00* (2006.01)
(52) U.S. Cl.
USPC .......................................................... 604/82

(58) Field of Classification Search
USPC ................ 604/82, 89, 104, 158, 162, 164.04, 604/164.08, 165.01, 165.02, 165.03, 165.04, 604/191, 192, 239, 240, 258
See application file for complete search history.

(56) References Cited

U.S. PATENT DOCUMENTS

| | | | |
|---|---|---|---|
| 5,322,510 A * | 6/1994 | Lindner et al. | ................... 604/82 |
| 5,437,292 A | 8/1995 | Kipshidze et al. | |
| 6,161,730 A | 12/2000 | Heusser et al. | |
| 2005/0096588 A1 | 5/2005 | Hagmann et al. | |
| 2007/0016128 A1 | 1/2007 | Keller | |

FOREIGN PATENT DOCUMENTS

| | | |
|---|---|---|
| DE | 39 00 635 | 7/1990 |
| WO | WO 03/039375 A2 | 5/2003 |
| WO | WO 2004100798 A1 | 11/2004 |

* cited by examiner

*Primary Examiner* — Theodore Stigell
*Assistant Examiner* — Brooke Matney
(74) *Attorney, Agent, or Firm* — Foley & Lardner LLP

(57) ABSTRACT

A dispensing assembly for two components including a double syringe, a mixer, and a transfer device interposed between the double syringe and the mixer. The transfer device (3) includes a transfer unit with a transfer tube having a mixer at one end and a coupling area with an inlet portion at the other end. The coupling area is provided with coupling means which cooperate with coupling means on the double syringe. At least around the coupling area of the transfer unit, a support is arranged which is attachable to the double syringe.

17 Claims, 3 Drawing Sheets

DISPENSING ASSEMBLY FOR TWO COMPONENTS WITH DOUBLE SYRINGE AND MIXER

Figure 1:
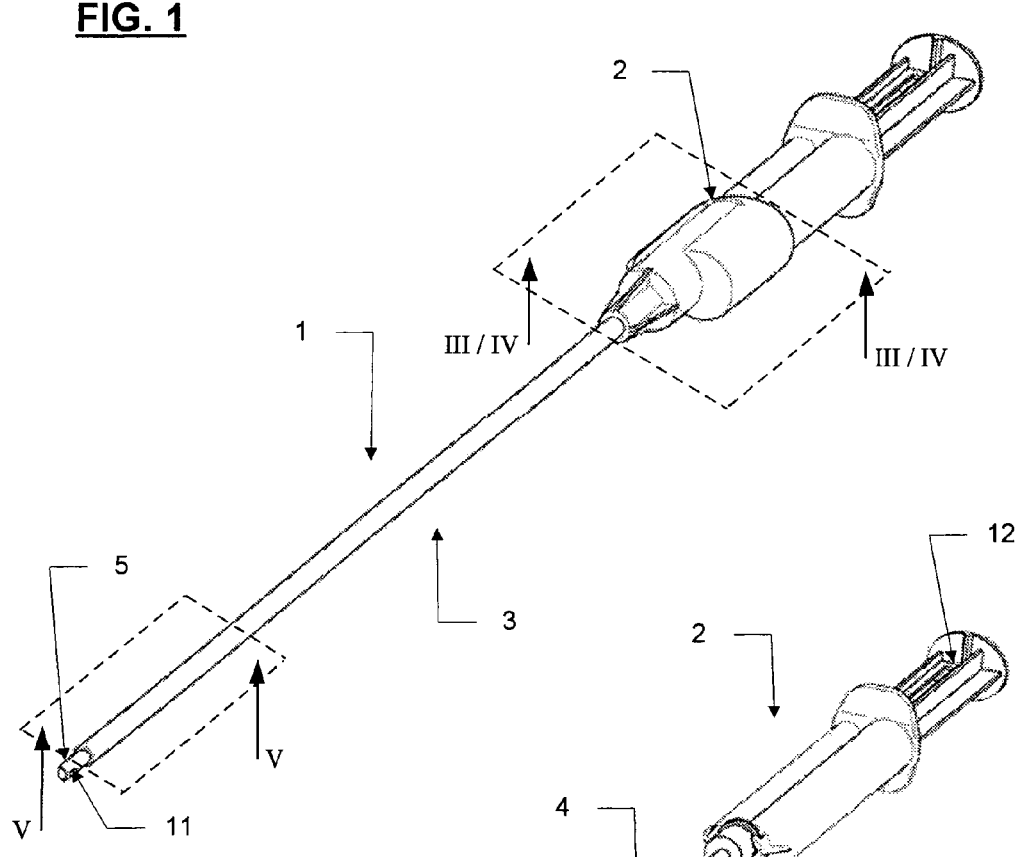

This application is the National Phase of PCT/CH2008/000261, filed Jun. 6, 2008, which claims priority to Switzerland Application No. 00938/07, filed Jun. 13, 2007, the disclosures of which are hereby incorporated by reference in their entirety.

The present invention relates to a dispensing assembly for at least two liquid components comprising a double syringe, a dispensing cartridge or dispensing device and a mixer according to the preamble of claim 1.

In most dispensing assemblies, the mixer is fastened to the cartridge and the assembly is used in this form. Often an accessory is attached to the mixer to influence the shape of the mixed components and to allow a targeted application of the material to the intended location in special situations. However, there are a number of applications, especially in medicine, where such a simple assembly of a double syringe, a mixer, and an accessory device is insufficient.

In medicine, it is now common practice to use two component adhesives to stop hemorrhages, to seal cuts and sutures, or to glue soft tissue. Thus, for example, the application of dispensing assemblies in operations involving the use of an endoscope requires a long transfer portion between the double syringe and the mixer, particularly in the case of laparoscopy. In laparoscopic operation techniques, relatively long tubes are required so that the distance between the double syringe and the dispensing tip is quite large.

WO 2004/100798 A1 to the applicant of the present invention discloses a dispensing assembly or a laparoscopic dispensing device according to the preamble of claim 1. This arrangement represented an improvement over the then known laparoscopic assemblies, particularly through the use of a mixer at the dispensing end. According to this solution, the mixer can be disassembled from the transfer tube, thereby requiring a relatively complex construction.

WO-A2-03/039375 and U.S. Pat. No. 2005/0096588 A1 disclose a spray device for laparoscopy comprising a tubular transfer portion adapted to be coupled with a dispensing device on its inlet side and with a spray device on its outlet side, the spray device being preceded by a mixing chamber having a flexible mixing member. The tubular transfer portion has two longitudinal channels.

U.S. Pat. No. 6,161,730 A discloses a dispensing assembly with a mixer which is connected via a transition piece connecting the outlets of the cartridge with the inlet of the mixer thus that the mixer can be put in any rotational position in view of the cartridge.

On the background of this prior art, it is the object of the present invention to provide a dispensing assembly, particularly for laparoscopy, where a double syringe, dispensing cartridge, or dispensing device is connected by means of a transfer portion to a relatively remote mixer while a simple but solid and cost-efficient construction is desired. This is accomplished by the assembly as described in claim 1.

The invention will be explained in more detail hereinafter with reference to drawings of an exemplary embodiment.

Figure 2:
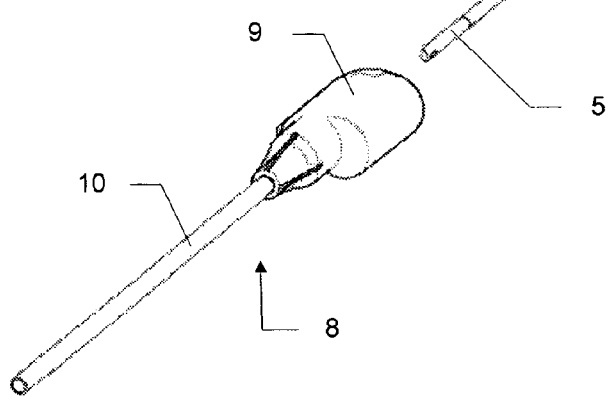

FIG. 1 shows a first exemplary embodiment of a laparoscopic assembly according to the invention in a perspective view, FIG. 2 shows the assembly of FIG. 1 prior to being fitted together.

Figure 3:
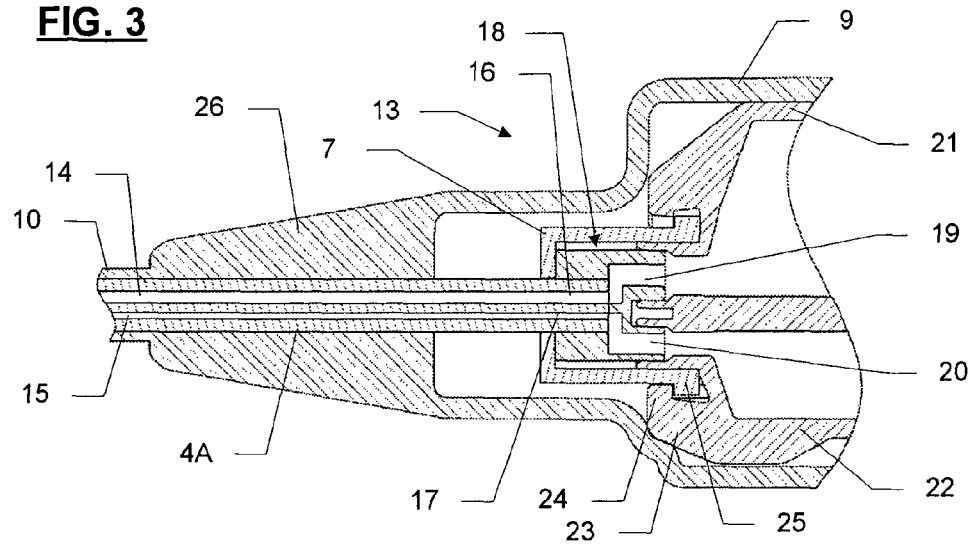
Figure 4:
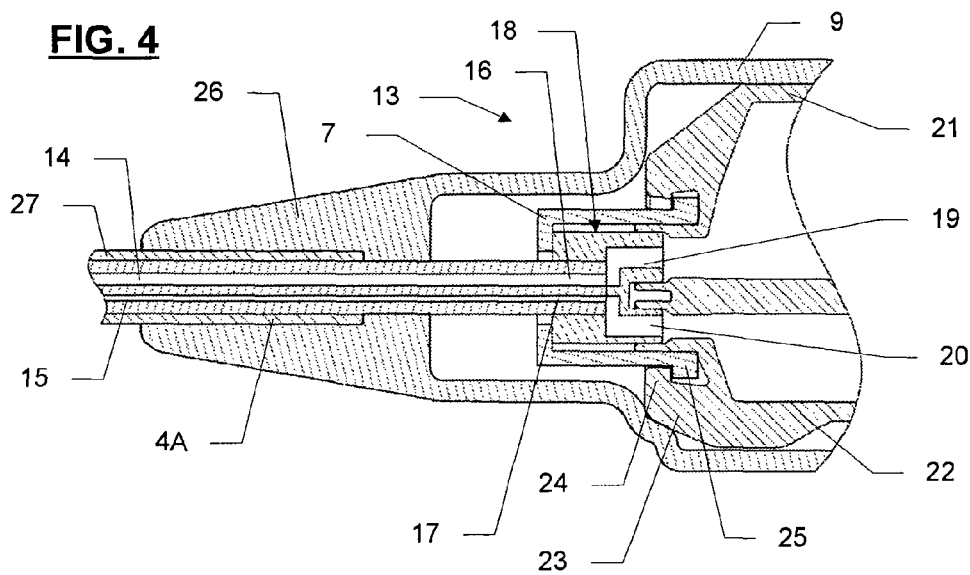
Figure 5:
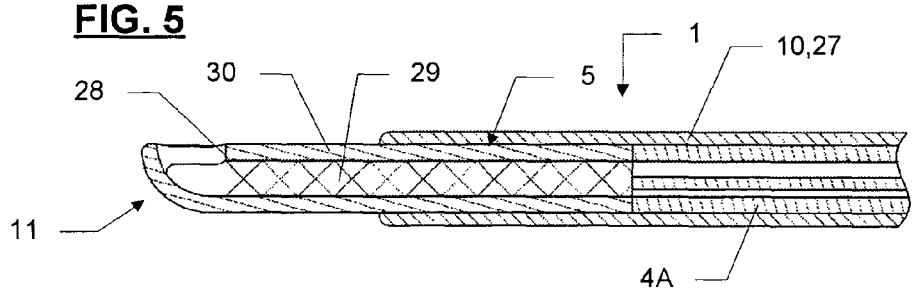
Figure 6:
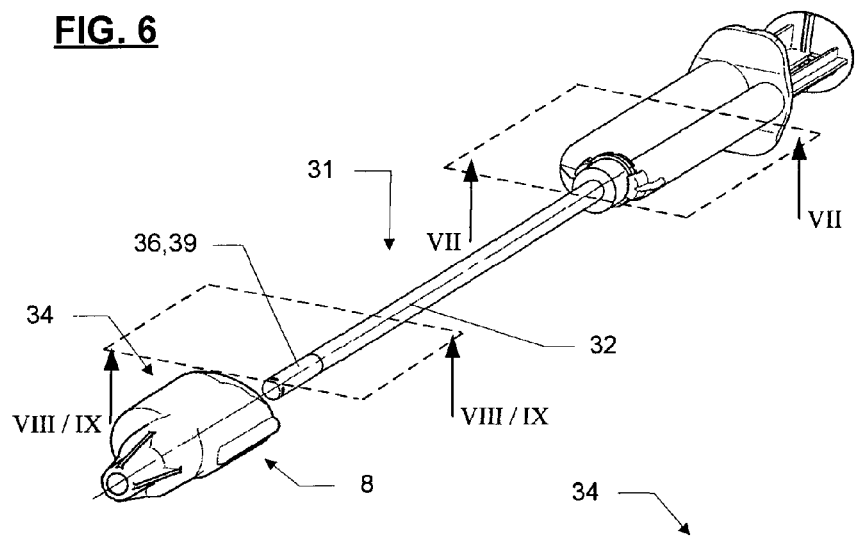
Figure 7:
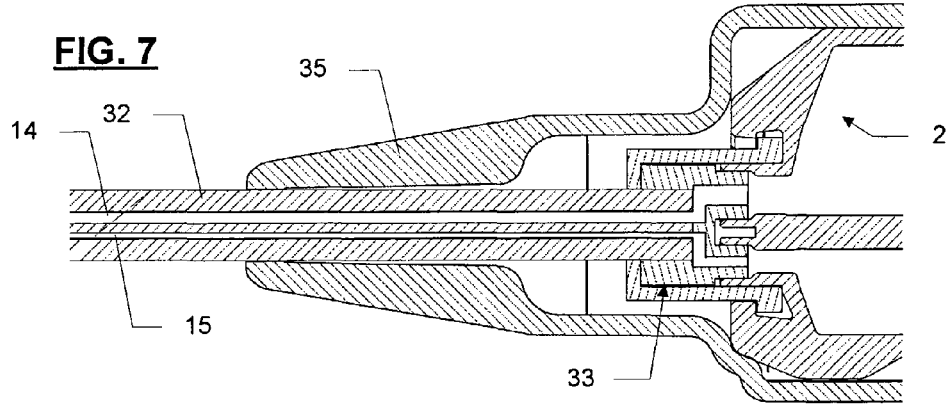
Figure 8:
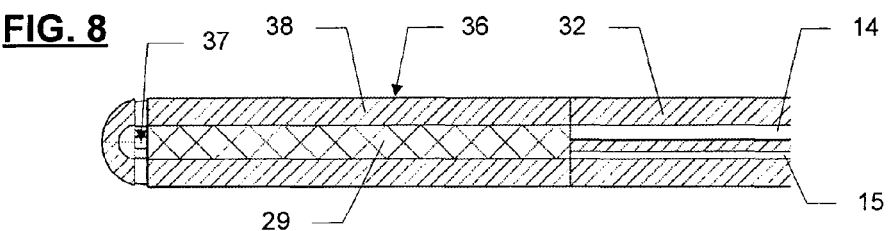
Figure 9:
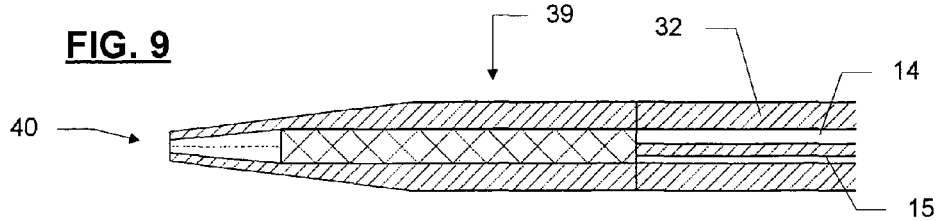

FIG. 3 shows the transfer portion and double syringe coupling area in an enlarged detail in a sectional view according to plane III-III in FIG. 1, FIG. 4 shows a variant of the embodiment of FIG. 3, FIG. 5 shows the dispensing end of the assembly of FIG. 1 in an enlarged detail in a sectional view according to plane V-V in FIG. 1, FIG. 6 shows a second exemplary embodiment of a laparoscopic assembly in a perspective view, FIG. 7 shows the transfer portion and double syringe coupling area in an enlarged detail in a sectional view according to plane VII-VII in FIG. 6, FIG. 8 shows the mixer end of the assembly of FIG. 6 in a sectional view according to plane VIII-VIII in FIG. 6, and FIG. 9 shows a variant of the mixer end of the assembly of FIG. 6.

The first exemplary embodiment of dispensing assembly 1 for laparoscopy comprises, see particularly FIGS. 1 and 2, a double syringe 2 and a transfer device 3 including a transfer unit 4 with a transfer tube 4A having a mixer 5 attached thereto at one end and a coupling area 6 at the other end. Preferably, the mixer is connected to the transfer tube in a non-detachable manner. The transfer unit is attachable to the double syringe by means of a bayonet ring 7. Around coupling area 6 and around transfer tube 4A, a support 8 is arranged which in this exemplary embodiment is formed of a support cap 9 to which a supporting tube 10 is fastened. As shown in FIG. 1, support cap 9 is pushed onto the double syringe and outlet 11 of mixer 5 extends beyond supporting tube 10. The double syringe is actuated by a double plunger 12.

Alternatively, a double cartridge or another dispensing device may be used instead of a double syringe. Hereinafter, the term double syringe will be used for the sake of simplicity.

FIG. 3 shows a cross-section according to plane III-III in FIG. 1 on an enlarged scale. This cross-section illustrates coupling area 6 of the transfer tube on the cartridge and fastening area 13 of the support cap on the double syringe. Inside transfer tube 4A, two separate channels 14 and 15 are arranged which on the syringe side open into two inlets 16 and 17 that are arranged in inlet portion 18 and communicate with outlets 19 and 20 of the double syringe. The two outlets and thus also the two inlets as well as the transfer channels may have equal diameters or different diameters, respectively. In the present example, outlet 19 of storage container 21 of the double syringe has a larger diameter than outlet 20 of storage container 22. Outlet flange 23 of double syringe 2 is provided with a bayonet socket 24 for receiving bayonet tabs 25 on bayonet ring 7.

In the present exemplary embodiment, first support 8 according to FIG. 3 is composed of support cap 9 and of an intermediate portion 26 on which supporting tube 10 is arranged. Here, the cap, the intermediate portion and the supporting tube are made in one piece of plastics material or metal.

In the embodiment variant according to FIG. 4, all parts are identical to those of FIG. 3 except for the attachment of supporting tube 27 which is fastened inside intermediate portion 26 by gluing, welding or the like.

In FIG. 5, the outlet end is illustrated in a cross-section according to plane V-V in FIG. 1, supporting tube 10 or 27 and the end of transfer tube 4A being visible. The transfer tube is followed by a mixer 5 that extends partially beyond supporting tube 10 or 27, its outlet 28 being arranged laterally, i.e. perpendicularly to sectional plane V-V in the embodiment according to FIG. 5.

FIGS. 6 to 9 show a second exemplary embodiment of a laparoscopic assembly, this assembly 31 including the same double syringe 2 and double plunger and the same bayonet coupling means as in the preceding exemplary embodiment.

One difference with respect to the previous exemplary embodiment is that transfer tube 32 has a greater wall thickness than transfer tube 4A and thus a higher rigidity.

Channels 14 and 15 are the same as in the previous example. Due to the greater wall thickness, transfer tube inlet portion 33 is not identical to inlet portion 18 of the previous example whereas inlets 19 and 20 are the same.

In this case, the support merely consists of support cap 34 and intermediate portion 35. In the present exemplary embodiment, the support provided by cap 34 is sufficient as the transfer tube has a sufficient rigidity. Mixer 36 with mixing elements 29 has outlets 37 that are arranged in housing 38 radially, as appears in FIG. 8.

In FIG. 9, a mixer 39 having a commonly used axial outlet 40 is depicted.

Within the scope of the above disclosure, different variations are possible. Thus, instead of the bayonet coupling by means of a ring, the attachment of the coupling area may be obtained by a snap-in, a push-on or a screw connection.

Fitting together the assembly is very simple: First, by means of the bayonet ring, the transfer tube with the mixer is attached, and then the support along with the support cap and possibly with the supporting tube is pushed over the transfer tube onto the double syringe and fastened thereto. The attachment may be obtained by a simple friction fit or by snap-in elements or the like.

The support may be reused whereas the inner part, i.e. the transfer tube with the mixer, is discarded after each application. The material is generally a suitable plastics material, but certain parts may also be made of metal.

The invention claimed is:

1. A dispensing assembly for at least two liquid components, comprising:
   a multicomponent syringe, cartridge or dispensing device;
   a transfer device connecting to the multicomponent syringe, cartridge or dispensing device, the transfer device comprising a transfer unit and a mixer, the transfer unit including a coupling area and a transfer tube, wherein the transfer tube includes at least two channels and is connected to the mixer at one end and to the coupling area at the other end, and wherein the coupling area includes transfer device coupling elements configured to cooperate with multicomponent coupling elements on the multicomponent syringe, cartridge or dispensing device; and
   a support, the support being a separate element from the transfer device and configured to be pushed over the transfer tube onto the multicomponent syringe, cartridge or dispensing device so as to be arranged at least around the coupling area of the transfer unit, the support comprising a support cap configured to attach to the multicomponent syringe, cartridge or dispensing device and a supporting tube fastened to the support cap, the supporting tube surrounding the transfer tube and a part of the mixer when the support cap is attached to the multicomponent syringe, cartridge or dispensing device, an outlet of the mixer extending beyond the supporting tube.

2. The dispensing assembly according to claim 1, wherein the coupling elements are bayonet coupling elements that include a bayonet ring.

3. The dispensing assembly according to claim 1, wherein the coupling elements include a snap-in, push-on or screw connection.

4. The dispensing assembly according to claim 1,
   wherein the mixer includes a mixer outlet and a mixer housing,
   wherein the mixer is elongated along a longitudinal axis, and
   wherein the mixer outlet is laterally positioned in the mixer housing relative to the longitudinal axis.

5. The dispensing assembly according to claim 4, wherein the mixer includes outlets radially positioned on the circumference of the mixer housing.

6. The dispensing assembly according to claim 1, wherein the mixer includes an axial outlet.

7. The dispensing assembly according to claim 1,
   wherein the multicomponent syringe, cartridge or dispensing device includes outlets, and
   wherein the at least two channels include inlets that communicate with the outlets of the multicomponent syringe, cartridge or dispensing device.

8. The dispensing assembly according to claim 1, wherein a length and a diameter of the transfer tube as well as the end of the transfer tube that includes the mixer are dimensioned to be placed within a laparoscopic tube.

9. The dispensing assembly according to claim 1, wherein the support cap includes a shape that is configured to be pushed over the multicomponent syringe, cartridge or dispensing device.

10. The dispensing assembly according to claim 1, wherein the transfer tube and the mixer are a unitary structure.

11. The dispensing assembly according to claim 1, wherein the support acts as a support for the transfer device.

12. The dispensing assembly according to claim 1, wherein the at least two channels have different diameters.

13. The dispensing assembly according to claim 1, wherein the support cap is configured to surround part of the multicomponent syringe, cartridge or dispensing device.

14. The dispensing assembly according to claim 1, wherein the supporting tube and the support cap comprise one piece.

15. The dispensing assembly according to claim 1, wherein the supporting tube is configured to form a unitary structure with the support cap.

16. The dispensing assembly according to claim 1, wherein a diameter of the supporting tube is smaller than a diameter of the support cap.

17. The dispensing assembly according to claim 1, wherein the mixer partially extends beyond the supporting tube.

\* \* \* \* \*